(12) United States Patent
Menassa

(10) Patent No.: US 9,067,019 B2
(45) Date of Patent: Jun. 30, 2015

(54) NEEDLELESS INJECTOR

(75) Inventor: Karim Menassa, Montreal (CA)

(73) Assignee: Medical International Technologies (MIT Canada) Inc., Montreal (CA)

( * ) Notice: Subject to any disclaimer, the term of this patent is extended or adjusted under 35 U.S.C. 154(b) by 83 days.

(21) Appl. No.: 13/261,314

(22) PCT Filed: Jan. 7, 2011

(86) PCT No.: PCT/CN2011/070092
§ 371 (c)(1),
(2), (4) Date: Jun. 6, 2012

(87) PCT Pub. No.: WO2011/082685
PCT Pub. Date: Jul. 14, 2011

(65) Prior Publication Data
US 2012/0253272 A1   Oct. 4, 2012

Related U.S. Application Data

(60) Provisional application No. 61/282,257, filed on Jan. 8, 2010.

(51) Int. Cl.
*A61M 5/30* (2006.01)
*A61M 5/31* (2006.01)
*A61M 5/32* (2006.01)
*A61M 5/50* (2006.01)

(52) U.S. Cl.
CPC ............. *A61M 5/30* (2013.01); *A61M 5/3134* (2013.01); *A61M 5/3293* (2013.01); *A61M 5/5086* (2013.01); *A61M 2205/583* (2013.01)

(58) Field of Classification Search
CPC .............. A61M 5/30; A61M 5/3007; A61M 2005/3104; A61M 5/484; A61M 5/31525; A61M 5/31593; A61M 5/3134; A61M 5/3293; A61M 3/0279; A61M 31/00
See application file for complete search history.

(56) References Cited

U.S. PATENT DOCUMENTS

| | | | |
|---|---|---|---|
| 3,805,783 A * | 4/1974 | Ismach | 604/71 |
| 7,357,781 B2 * | 4/2008 | Menassa | 604/70 |
| 2006/0178627 A1 * | 8/2006 | Geiger et al. | 604/111 |
| 2009/0283493 A1 * | 11/2009 | Witowski | 215/258 |

* cited by examiner

*Primary Examiner* — Nicholas Lucchesi
*Assistant Examiner* — Weng Lee
(74) *Attorney, Agent, or Firm* — George A. Seaby

(57) ABSTRACT

A pistol-shaped needleless injector includes a readily replaceable barrel (36) in the front end thereof facilitating adjustment of the dosage administered using the injector. A disposable nozzle (98) mountable on a holder (97) extending outwardly from the front discharge end of the barrel (36) provides an indication that the nozzle (98) has been used and should be discarded.

13 Claims, 6 Drawing Sheets

NEEDLELESS INJECTOR

This application claims the benefit of Provisional Application Serial No. 61/282,257, filed Jan. 8, 2010, and titled "NEEDLELESS INJECTOR".

FIELD OF THE INVENTION

This invention relates to a needleless injector.

DESCRIPTION OF RELATED ART

In particular, the present invention relates to a needleless injector of the type described in the inventor's U.S. Pat. No. 7,357,781, issued Apr. 15, 2008, which is incorporated herein by reference. While the basic structure of the invention disclosed herein is similar in many respects to the patented injector, the new injector described herein includes several important improvements over the patented injector.

Injectors of the type described herein are commonly used to inject large numbers of humans or animals such as pigs and chickens. Depending upon the nature of the composition being injected and/or the size of the animal rather than having a plurality of different injectors, it is advantageous to be able to readily change the dosage of a single injector. Moreover, in order to avoid cross-contamination during mass injections, the nozzle of the injector should be readily replaceable and preferably include some form of indicator that it has not been used already.

BRIEF SUMMARY OF THE INVENTION

Accordingly, one aspect of the invention is a needleless injector comprising:
  a barrel for receiving an injectable liquid from a source thereof;
  a holder extending outwardly from one end of said barrel;
  a disposable nozzle removably mounted on said holder for discharging liquid from said holder and barrel;
  a plunger slidable in said barrel for movement between a retracted position in which liquid is drawn into said barrel between said holder and said plunger and an extended position in which liquid is discharged through said holder and disposable nozzle;
  a piston slidable in said barrel movable under fluid pressure to move said plunger to an extended, liquid discharge position;
  a retractor connected to said piston in said barrel for moving said plunger to the retracted position when said piston is retracted;
  a coupler connecting said retractor to said plunger permitting sliding of said piston in said barrel against said plunger to move the latter to the extended position, and for drawing the plunger to the retracted position when the piston and retractor are moved in a direction away from said holder and nozzle to the retracted position;
  a first valve for introducing fluid under pressure into said barrel alternately on one side of said piston to move the piston and plunger from the retracted to the extended position to discharge liquid through said holder and nozzle, and on a second side of said piston to return the piston and plunger to a retracted position in which injectable liquid is drawn into the barrel between said holder and nozzle and said plunger;
  a trigger for operating said first valve to cause said plunger to move from the retracted to the extended position and then back to the retracted position each time the trigger is operated; and
  a stop in a second end of said barrel remote from said one end for limiting movement of the piston when the plunger and piston move to the retracted position.

In accordance with a second aspect the invention is a disposable nozzle for use with the above described injector comprising an elongated tubular body having
  a tapering front discharge end;
  a passage extending through said body for discharging liquid received from said holder;
  an annular recess in a rear end of said body for receiving an annular holder sleeve; and
  a resilient detent extending outwardly from an inner wall of said recess for extending into a notch in a front end of the holder sleeve when the nozzle is mounted on the holder, whereby, when the nozzle is rotated to remove it from the holder, the detent breaks off providing an indication that the nozzle has been used.

Like the inventor=s patented injector, the injector of the present invention is relatively simple and can be used to carry out a plurality of successive injections quickly. Moreover, by incorporating a readily replaceable barrel structure, the injector of the present invention provides a mechanism for quick and easy adjustment of the dosage of the injector.

The present invention also provides a replaceable nozzle, which is easy to attach and remove from the discharge end of a needleless injector, and which provides and indication that the nozzle has been previously used.

BRIEF DESCRIPTION OF THE DRAWINGS

The above-mentioned and other novel features of the invention are described hereinafter in greater detail with reference to the accompanying drawings, wherein.

DETAILED DESCRIPTION OF THE INVENTION

Figure 1:
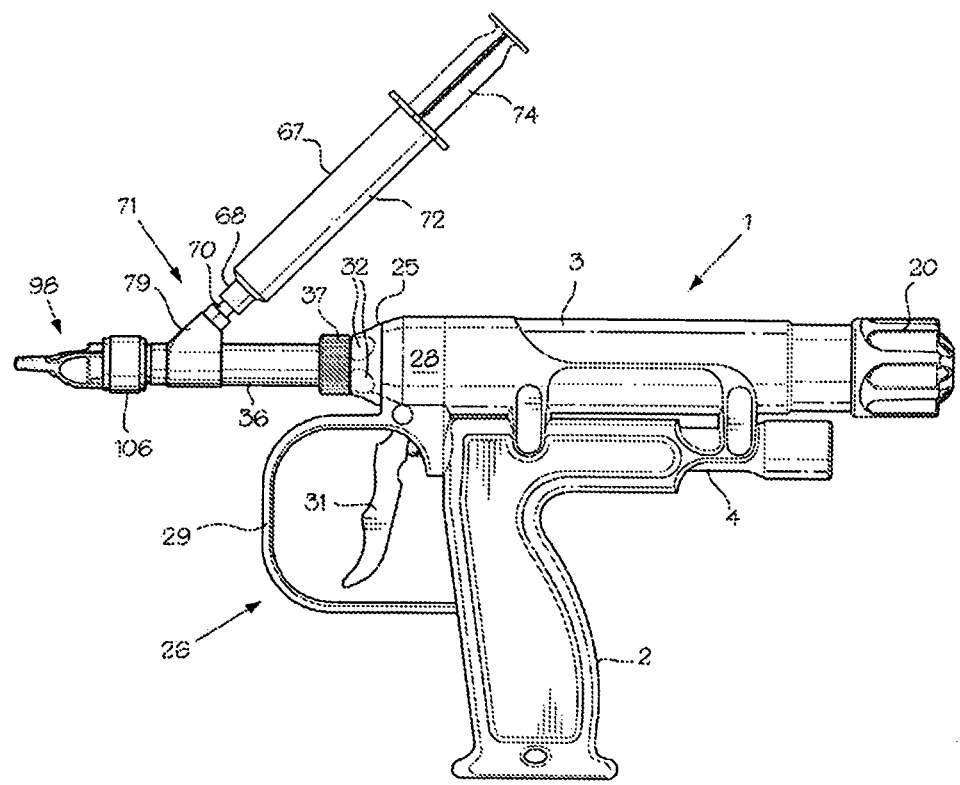
FIG. 1 is a side view of a needleless injector in accordance with the present invention.
Figure 2:
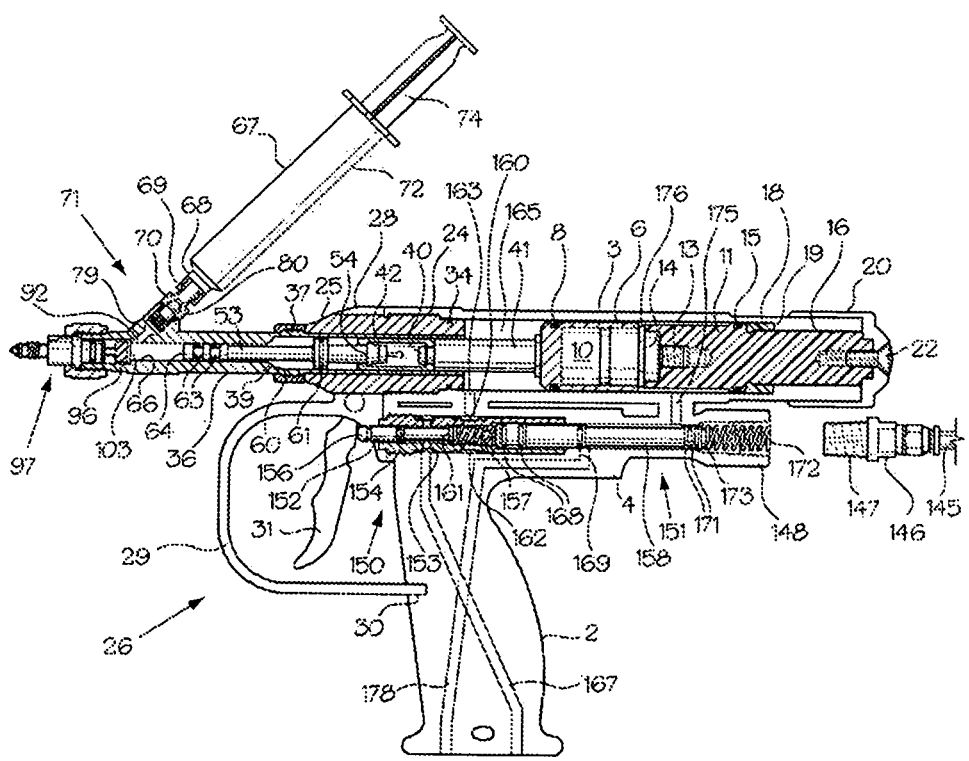
FIG. 2 is a longitudinal sectional view of the injector of FIG. 1 with parts omitted.

With reference to FIGS. 1 and 2, the injector of the present invention is in the shape of a pistol and includes a plastic body indicated generally at 1 with a handle 2 extending outwardly therefrom. The body contains upper and lower cylinders 3 and 4, respectively containing most of the remaining elements of the injector.

A brass piston 6 is slidably mounted in the upper cylinder 3. An O-ring 8 seals the piston 6 in the cylinder 3. The piston 6 is generally cup-shaped, including a rear recess 9 (FIG. 4) containing a cylindrical permanent magnet 10. The piston 6 and the magnet 10 are retained in a rest or start position in the cylinder 3 by a plastic plug 11 containing a steel bolt 13, the head 14 of which abuts the magnet 10. The plug 11 is sealed in the cylinder 3 by an O-ring 15 (FIG. 2).

The threaded rear end 16 of the plug 11 carries a spacer ring 18 which abuts a shoulder 19 in the cylinder 3 for limiting rearward movement of the plug 11 and consequently the piston 6 in the cylinder 3. By rotating the plug 11, the gap between the spacer ring 18 and the shoulder 19 is changed, thus changing the stroke of the piston 6. The plug 11 is rotated using a generally cup-shaped knob 20 rotatably mounted on the rear end of the cylinder 3. A bolt 22 secures the knob 20 on the plug 11. Thus, the plug 11 acts as a stop for the piston 6 and forms part of a stroke adjusting mechanism for the injector.

The externally threaded rear end 24 of the plastic sleeve 25 mates with the internally threaded front end of the cylinder 3. The sleeve 25 carries a trigger assembly indicated generally at 26 (FIGS. 1 and 2). A flange 27 (FIG. 4) on the sleeve 25 retains the trigger assembly against the front end of the cylinder 3. The trigger assembly 26 is defined by a collar 28 around the sleeve 25, a generally C-shaped finger guard 29 integral with the collar 28 and extending downwardly from the collar 28 into a recess 30 (FIG. 3) in the front of the handle 2, and a trigger 31. Concave grooves 32 (FIGS. 1 and 4) in the front end of the sleeve 25 facilitate gripping of the sleeve for screwing it into the cylinder 3 and for removing it from the cylinder.

O-rings 34 seal the sleeve 25 in the cylinder 3. The rear end of the sleeve 25 is internally threaded for connecting the threaded rear end 35 of a barrel 36 to the sleeve. The barrel 36 is centered in the sleeve 25 by an internally threaded annular cap 37 which is threaded onto external threads 38 (FIG. 4) on the barrel. With the structure illustrated, the barrel 36 can readily be replaced with a smaller or larger barrel depending upon the dosage to be administered. In order to remove the barrel 36 from the front end of the upper cylinder 3 of the body 1, it is merely necessary to rotate the barrel so that the threaded rear end 35 disengages from the internally threaded sleeve 25. The barrel 36 can then be pulled out of the sleeve 25. A barrel 36 for a very small dosage includes a hole 39 (FIG. 2), the purpose of which is described hereinafter. A head 40 on the front end of a retractor 41 (FIG. 4) is snap fitted into the rear end of a coupler 42 in the rear end of the barrel 36. The rear end 43 of the retractor 41 is slid onto the narrow diameter front end 44 of the piston 6. The front end of the retractor 41 includes a reduced diameter neck 47 (FIG. 4) and the head 40, which has a larger diameter than the neck. The head 40 and neck 47 secure the front end of the retractor 41 in the tubular coupler 42.

Figures 3, 4:
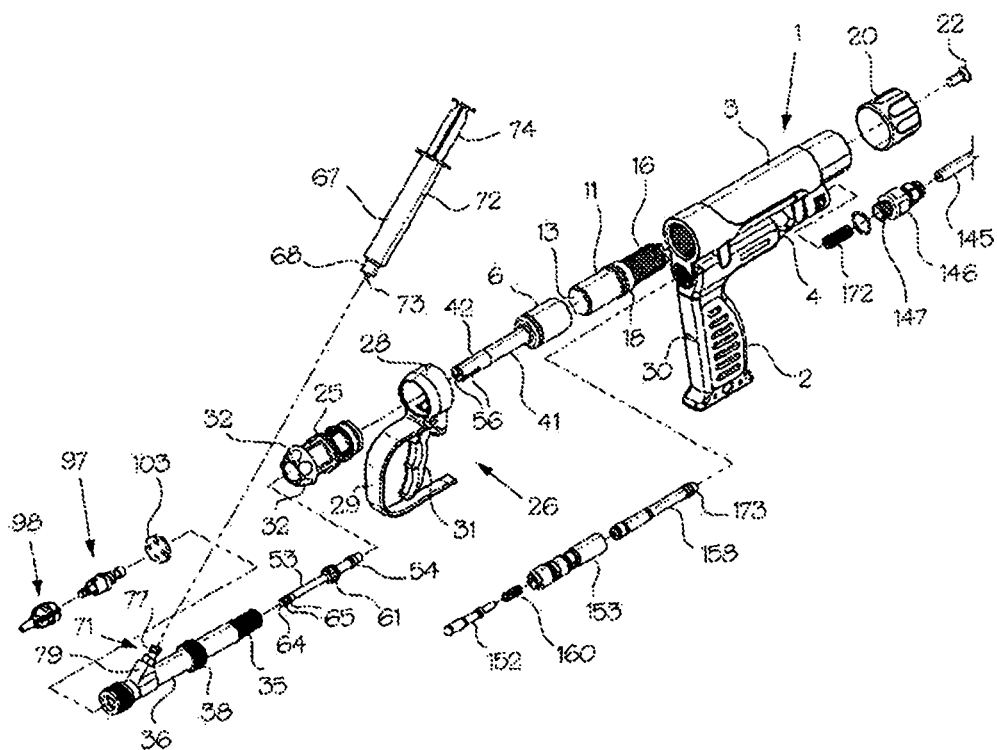
FIG. 3 is an exploded, isometric view of the injector of FIGS. 1 and 2.
FIG. 4 is an exploded, partly sectioned view of most of the principle elements of the injector of FIGS. 1-3.

As best shown in FIG. 4, the coupler 42 includes inwardly extending annular flanges 51 and 52 at its rear and front ends, respectively. The front end of the retractor 41 is held by the rear flange 51 of the coupler 42 so that movement of the piston 6 and the retractor 41 results in corresponding movement of the coupler 42. During assembly, the head 40 of the retractor 41 is forced into the flexible rear end of the coupler 42 until the flange 51 snaps into position in the neck 47 behind the head 40. Also during assembly, the rear end of a plunger 53 is inserted into the front end of the coupler 42 a sufficient distance that an annular flange 54 on the plunger enters the coupler. During rearward movement of the coupler 42, the flange 52 engages the flange 54 on the rear end of the plunger 53. Three longitudinally extending slots 56 spaced equidistant apart in the front end of the coupler 50 make the front end flexible to facilitate sliding of the plunger relative to the coupler and sliding of the coupler in the barrel 36. When the retractor 41 moves forwardly, it pushes the coupler 42 forwardly in the barrel 36 so that the front end of the retractor 42 engages the rear end of the plunger 53 to force the plunger forwardly to effect an injection. Forward movement of the retractor 41 and the coupler 42 are limited by a shoulder 60 in the passage through the barrel 36. When the retractor 41 moves forwardly, a flange 61 on the plunger 53 comes into contact with the shoulder 60 which limits the stroke of the plunger 53. When the piston 6 and the retractor 41 are moved rearwardly, the retractor 41 retracts the coupler 42 and the plunger 53 to the start or rest positions. Seals 63 near the front end of the plunger 53 seal the head 64 of the plunger 53 in the narrower diameter front end of the barrel 36.

The head 64 of the plunger 53 slides in a chamber 66 (FIG. 2) in the reduced diameter front end of the barrel 36. Rearward movement of the plunger 53 in the barrel 36 creates a partial vacuum in the chamber 66 to draw medicine into the chamber from a syringe 67. The internally threaded neck 68 of the syringe 67 is connected to the externally threaded outer end 69 of the body 70 of a one-way valve indicated generally at 71 in FIGS. 1 and 2. The syringe 67 is a conventional plastic syringe including a barrel 72 with a plunger 74 slidable in one end thereof for discharging liquid through a narrow diameter nozzle 73 (FIG. 3) the other end thereof. The syringe barrel 72 includes a scale (not shown) indicative of the dosage injected each time the injector is operated. It will be appreciated that the syringe 67 can be replaced by a medicine bottle or bag.

Figure 5:
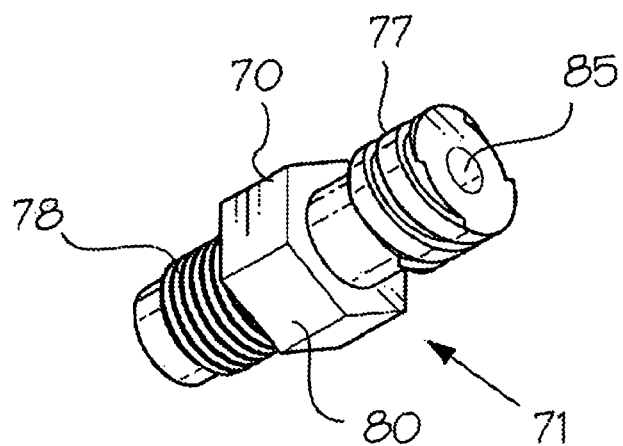
FIG. 5 is an isometric view of a valve used in the injector of FIGS. 1-4.
Figure 6:
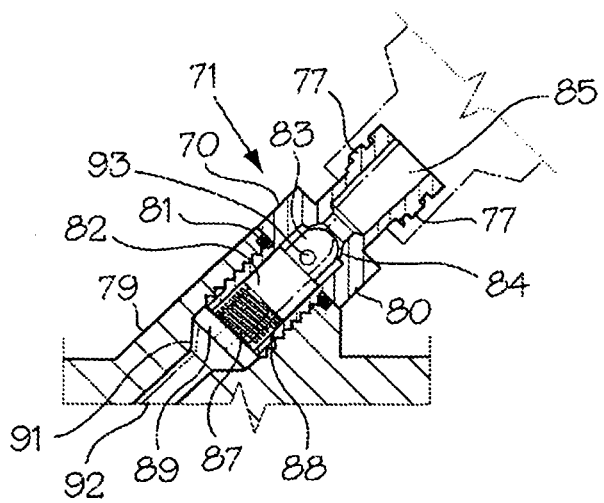
FIGS. 6 and 7 are longitudinal sectional views of the valve of FIG. 5.
Figure 7:
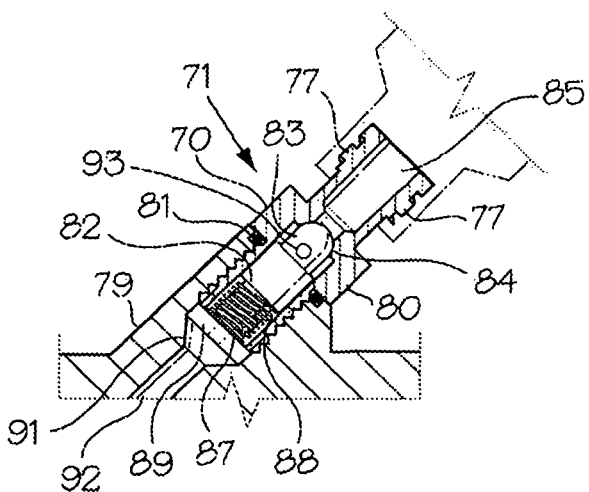

The liquid discharged through the syringe nozzle 73 passes through the one-way valve 71. As best shown in FIGS. 5 to 7, the valve 71 includes the tubular body 70 and a valve piston or stem 76 slidable in the body. The threaded outer end 77 of the valve body 75 is connected to the internally threaded neck 68 of the syringe 67, and the other threaded end 78 of the body is mounted in an internally threaded, rearwardly inclined inlet 79 integral with the barrel 36. The middle 80 of the body 75 is hexagonal in cross section for facilitating mounting the valve in the inlet 79 using a wrench. The valve body 75 is sealed in the inlet 79 by an O-ring 81.

A cylindrical valve stem 82 with a hemispherical top end 83 is slidable in the body 75 for seating against a tapered seat 84 in the passage 85 through the body. The stem 82 is biased to the closed position (FIG. 6) by a helical spring 87 on the narrow diameter bottom end of the stem. The spring 87 is compressed between a shoulder 88 on the stem 82 and a circular plate 89 seated on a shoulder 91 in the passage 92 through the inlet 79.

When the syringe plunger is pushed into the barrel 72, fluid flows from the syringe into the valve body 70 pushing the stem 82 away from the seat 84 to the open position (FIG. 7). Fluid flows through diametrically opposed holes 93 (one shown) in the stem 82 into a central passage (not shown) with a closed top end and an open bottom end. The fluid exits the stem and flows through an inlet passage 92 into the chamber 66 at the front end of the injector barrel 36.

When the plunger 53 is driven forward, the fluid is discharged from the barrel 36 via a valve 96, a nozzle holder 97 and a disposable plastic nozzle 98. The valve 96 is defined by a hollow valve stem 100 extending into a passage 101 through the tubular nozzle holder 97 and a cylindrical head 102 closing the inner end of the tubular stem 100. A circular, stainless steel spacer washer 103 is sandwiched between the valve head 102 and a shoulder 105 (FIG. 4) at the front end of the chamber 66. The nozzle holder 97 is held in the externally threaded front end 104 of the barrel 36 by an internally threaded cap 106.

Figure 8:
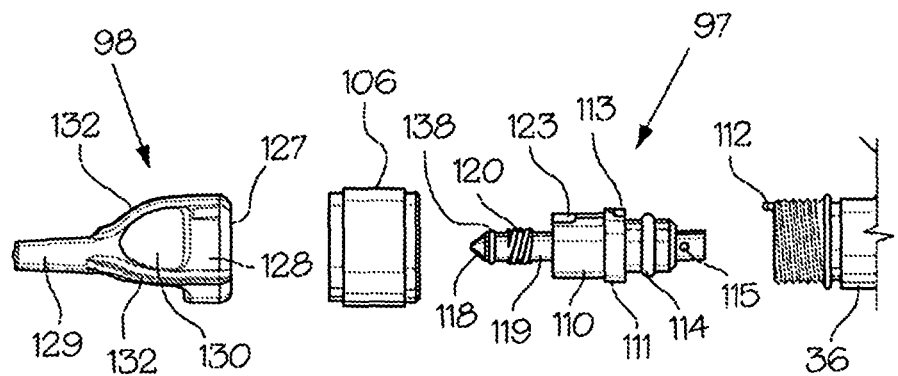
FIG. 8 is an exploded view of the discharge end of the injector of FIGS. 1 and 2.
Figure 9:
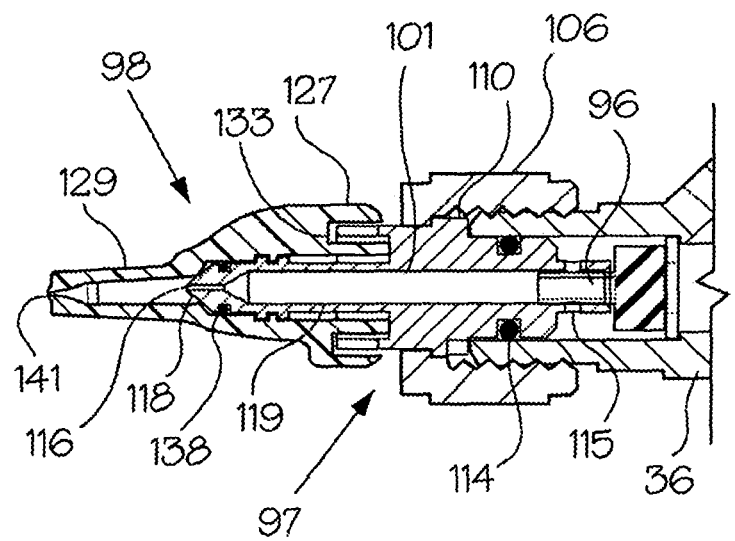
FIG. 9 is a longitudinal sectional view of the discharge end of the injector of FIGS. 1 and 2.
Figure 10:
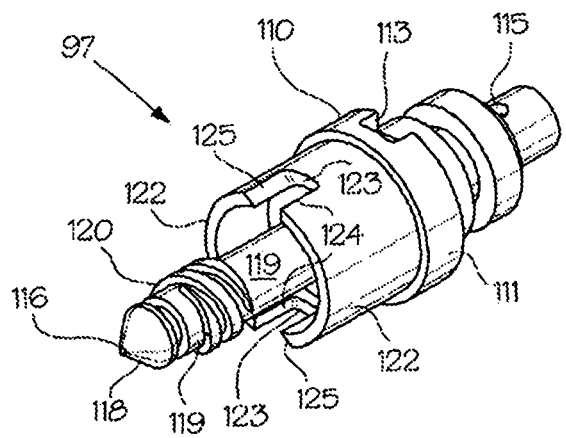
FIG. 10 is an isometric view of a nozzle holder used in the injector of FIGS. 1 and 2.
Figure 11:
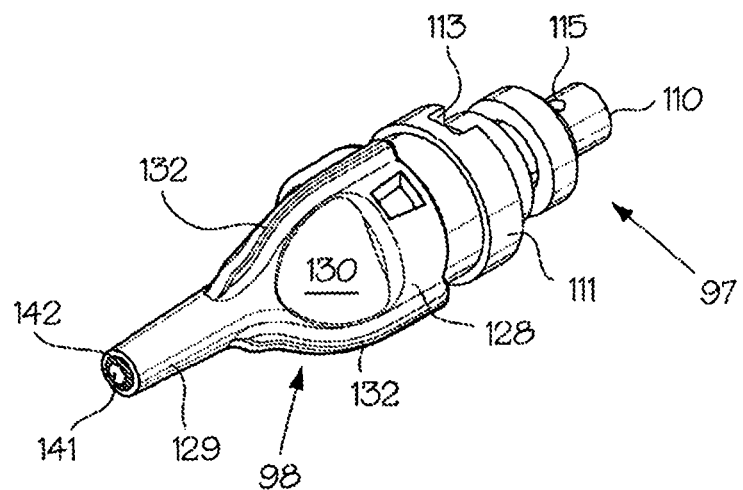
FIG. 11 is an isometric view of a disposable nozzle on the nozzle holder of FIG. 10.
Figure 12:
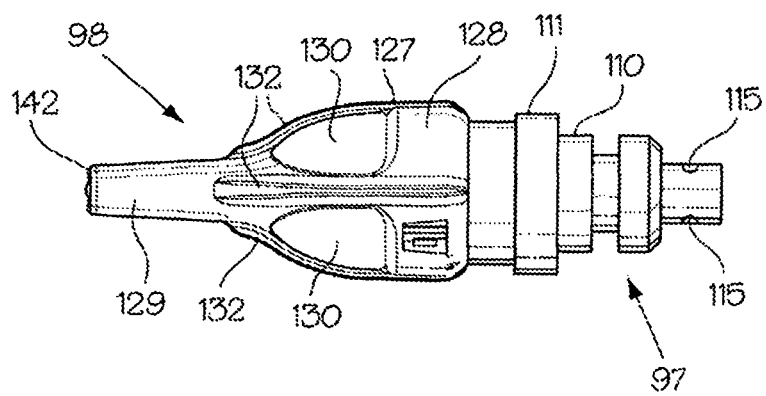
FIG. 12 is a side view of the disposable nozzle and holder of FIG. 11.

Referring to FIGS. 8 to 10, the holder 97 includes a tubular body 110 with the central, longitudinally extending passage 101 therethrough. When the holder 97 is slid into the barrel 36 an annular flange 111 proximate the center of the body 110 abuts the end of the barrel 36 to limit movement of the holder into the barrel. A finger 112 on the discharge end of the barrel 36 mates with a notch 113 in the flange 111 to prevent rotation of the holder in the barrel. An O-ring 114 seals the holder 97 in the barrel 36. Fluid passing through the valve 96 enters the passage 101 in the holder 97 via diametrically opposed holes 115 and is discharged through a small orifice 116 in the tapered outer end 118 (FIG. 7) of the cylindrical nozzle 119 at the discharge end of the body 110. Threads 120 are provided near the outer end of the nozzle 119. A cylindrical sleeve 122 extends outwardly around the inner end of the nozzle 119. Diametrically opposed notches 123 are provided in the outer free end of the sleeve 122. Each notch 123 includes one more or less radially extending, straight side 124 and one beveled side defining a knife edge 125.

The disposable nozzle 98 is defined by an elongated tubular body 127 with a cylindrical rear end 128. The body 127 tapers forwardly from the cylindrical rear end 128 to a small diameter ejection end 129. Three deep concave grooves 130 in the body 127 alternating with longitudinally extending ridges 132 facilitate manual manipulation of the nozzle 98.

Figure 13:
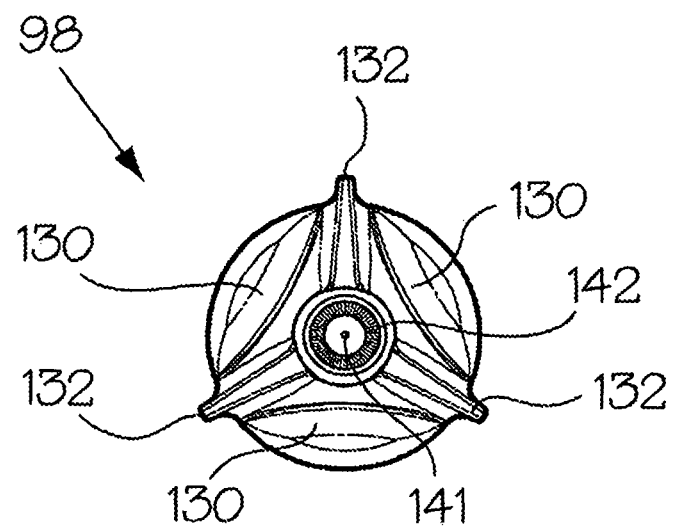
FIG. 13 is a front view of the nozzle of FIGS. 11 and 12.
Figure 14:
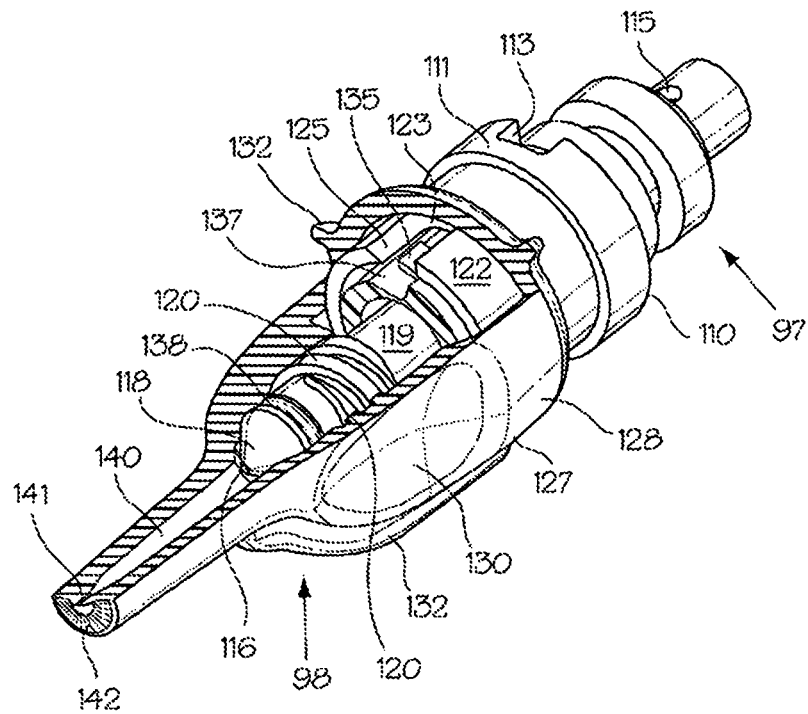
FIG. 14 is a partly sectioned isometric view of the nozzle holder and disposable nozzle of FIGS. 10-13.
Figure 15:
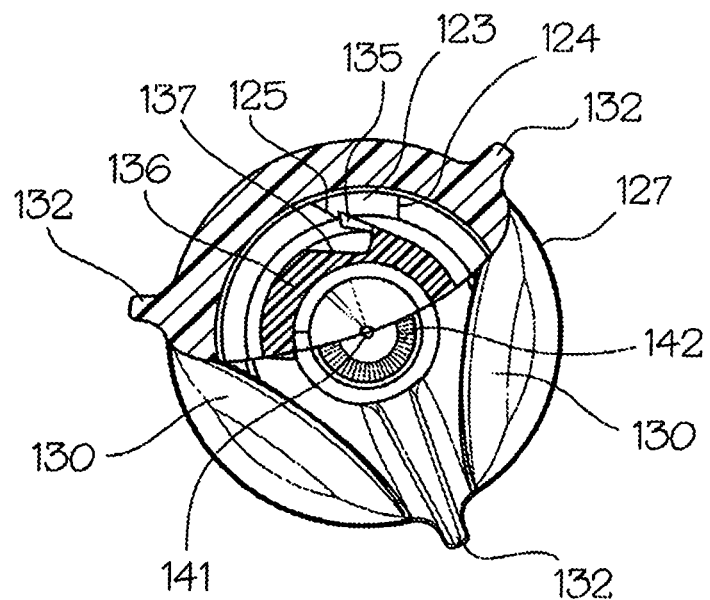
FIG. 15 is a partly sectioned front view of the nozzle holder and disposable nozzle of FIG. 14.

An annular recess 133 (FIG. 9) in the rear end 128 of the body 127 receives the sleeve 122 on the holder 97. A detent or finger 135 extends outwardly at an acute angle from the inner wall 136 of the recess 133. A longitudinally extending groove 137 in the wall 136 permits flexing of the detent 135. When the nozzle 98 is being screwed onto the holder 97 (by rotating the nozzle clockwise in FIGS. 13 and 14), the detent 135 enters one of the notches 123. During each half rotation of the nozzle 98, the detent 135 engages the edge 124 of a notch 123 and flexes into the groove 137. As best shown in FIGS. 14 and 15. when the nozzle 98 is fully on the holder 97, the detent 135 extends into one of the notches 123. The nozzle 98 is sealed on the holder 97 by an O-ring 138 (FIGS. 8 and 9).

Fluid ejected from the holder 97 passes through a tapering passage 140 and is discharged through a narrow ejection orifice 141. Alternating, radially extending ridges and grooves 142 on the discharge end of the nozzle body 127 grip the area around an injection site. Upon completion of each injection, the nozzle 98 is gripped between a thumb and index finger and rotated sharply in a counterclockwise direction. The detent 135, which extends into one of the notches 123, engages the knife edge 125. Continued rotation of the nozzle 98 in the same direction causes the detent 135 to break at its thinner end, i.e. the end attached to the remainder of the nozzle body 127. The detent 135 remains in the notch 123 and when the nozzle 98 is removed, the detent falls out of the notch. Thus, the detent 135 provides an audible indication that the nozzle has not been used. During mounting of the nozzle on the holder 97, each time the detent 135 flexes into a groove 137, a clicking noise occurs, indicating the detent is on the nozzle. If the detent 135 is absent, there would be no resistance to rotation of the nozzle 95 on the holder 97 and there would be no sound indicating that the detent 135 is intact.

Referring again to FIG. 2, injection is effected using compressed gas from a source (not shown) thereof when the trigger 31 is squeezed. The gas is fed into the lower cylinder 4 via a hose 145 and a connector 146, the externally threaded end 147 of which is threaded into the internally threaded rear end 148 of the cylinder 4. Squeezing of the trigger 31 opens front and rear valves indicated generally at 150 and 151, respectively. The front valve 150 includes a stern 152 slidable in a sleeve 153 in the lower cylinder 4. The stem 152 is sealed in the sleeve 153 by an O-ring 154. The hemispherical outer end 156 of the stem 152 extends out of the sleeve 153 into engagement with the trigger 31. The conical inner end 157 of the stem 153 abuts the front end of the stem 158 of the rear valve 151. The stem 153 is biased forwardly by a helical spring 160 sandwiched between an annular flange 161 on the stem 153 and the front end of the rear valve stem 158. When the trigger 31 is squeezed, the stem 153 moves rearwardly, whereby a diametrically extending passage 162 is aligned with a passage 163 through the lower cylinder 4 into the space 165 between the front end of the piston 6 and the rear end of the sleeve 25, whereby air in front of the piston 6 can be discharged through the valve 150 and a passage 167 in the handle 2 of the injector.

At the same time, the stem 152 pushes the stem 158 of the rear valve 151. The front end of the stem 158 is sealed in the rear end of the sleeve 153 by O-rings 168 and in the lower cylinder 4 by an O-ring 169. The rear end of the stem 158 is sealed in the rear end of the cylinder 4 by O-rings 171. The stem 158 is biased forwardly to the dosed position shown in FIG. 2 by a helical spring 172 sandwiched between an annular flange 173 on the rear end of the stem and threaded outlet end 147 of the connector 146 on the outlet end of the compressed air hose 145. When the stem 158 moves rearwardly, compressing the spring 172, the rear valve 151 is opened permitting air to flow around the flange 173 and through the valve 151 and a passage 175 into a chamber 176 behind the piston 6. When there is a sufficient pressure build-up in the chamber 176, the piston 6 is driven forward at which time air is discharged from the chamber 165 in front of the piston via the passages 160, 162 and 167, and the plunger 55 moves forwardly to discharge fluid from the chamber 66 through the valve 96, the holder 97 and the disposable nozzle 98. Once injection has been completed, the nozzle 98 is removed and replaced with a fresh nozzle.

When the trigger 31 is released, the springs 160 and 172 return the valve stems 152 and 158 to the rest or closed positions. Air behind the piston 6 is discharged via the passage 175, and passes around the rear valve stem 158 for venting through a second passage 178 in the handle 2.

When injecting very small dosages, the barrel 36 is replaced with a smaller barrel, i.e. a barrel with a smaller internal diameter having the small hole 39 therein. The hole 39 permits exhausting of air from the barrel 36 in front of the flange 60 on the plunger 55. In the absence of the hole 39 because of back pressure during injection, it would not be possible to accurately control the dosage when using a small barrel. As described hereinbefore, the barrel 36 is removed from the upper cylinder 3 of the body 1 by rotating the barrel so that the threaded rear end 35 disengages from the sleeve 25. Once the barrel 36 has been removed, the plunger 53 can be pulled out of the front end of the coupler 42 which, by virtue of the slots 56, is free to expand. The plunger 53 is replaced with a plunger having a smaller diameter matching the internal diameter of the smaller barrel. Of course, if a small diameter barrel is being replaced with a larger diameter barrel, the plunger 53 is replaced with a larger diameter plunger.

The invention claimed is:

1. A needleless injector comprising:
   a barrel for receiving an injectable liquid from a source thereof;

a holder including a first end extending into said barrel, a central passage for conveying liquid and a cylindrical sleeve at a second end extending out of said barrel;

a disposable, plastic nozzle removably mounted on the cylindrical sleeve of said holder for discharging liquid from said holder and barrel, said disposable nozzle including an elongated tubular body having a tapered front discharge end; a passage extending through said body for discharging liquid received from said holder; an annular recess in a rear end of said body for receiving the holder sleeve; and a resilient detent extending outwardly from an inner wall of said annular recess for extending into a notch in a front end of the holder sleeve when the nozzle is mounted on the holder;

a plunger slidable in said barrel for movement between a retracted position in which liquid is drawn into said barrel between said holder and said plunger and an extended position in which liquid is discharged through said holder and disposable nozzle;

a piston separate from said plunger slidable in said barrel movable under fluid pressure to move said plunger to an extended, liquid discharge position;

a retractor connected to said piston in said barrel for moving said plunger to the retracted position when said piston is retracted;

a coupler connecting said retractor to said plunger permitting sliding of said piston in said barrel against said plunger to move the latter to the extended position, and for drawing the plunger to the retracted position when the piston and retractor are moved in a direction away from said holder and nozzle to the retracted position;

a first valve for introducing fluid under pressure into said barrel alternately on one side of said piston to move the piston and plunger from the retracted to the extended position to discharge liquid through said holder and nozzle, and on a second side of said piston to return the piston and plunger to a retracted position in which injectable liquid is drawn into the barrel between said holder and said plunger;

a trigger for operating said first valve to cause said plunger to move from the retracted to the extended position and then back to the retracted position each time the trigger is operated; and a stop in a second end of said barrel remote from said one end for limiting movement of the piston when the plunger and piston move to the retracted position.

2. The needleless injector of claim 1 including a magnet in said piston releasably retaining the piston and plunger in the retracted position until the trigger is operated.

3. The needleless injector of claim 1, including a stroke adjuster for altering the stroke of said piston and consequently the dosage of liquid discharge from said barrel.

4. The needleless injector of claim 3, wherein said stroke adjuster includes a threaded plug in said second end of said barrel for engaging said piston, a shoulder in said second end of the barrel; and a spacer ring between said plug and said shoulder, whereby rotation of said plug in said barrel changes the gap between the shoulder and the plug, and consequently the length of the stroke of said piston.

5. The needleless inject of claim 4, wherein said stroke adjuster includes a knob rotatably mounted on said second end of said barrel and connected to said plug for rotating said plug; and a scale on said barrel exposed by movement of said knob to indicate a dosage setting of the injector.

6. The needleless injector of claim 1, including a removable cap on said one end of said barrel for retaining said holder in said barrel.

7. The needleless injector of claim 1, including a syringe on said barrel for carrying a supply of injectable liquid, and a scale on said syringe indicative of the dosage of liquid injected each time an injection is made using the injector.

8. The needless injector of claim 7, including a one-way valve connecting said syringe to the barrel for admitting injectable liquid into said barrel when the plunger is retracted.

9. The disposable nozzle of claim 1, wherein said body contains internal threads for engaging corresponding threads on the holder.

10. The disposable nozzle of claim 9, wherein said detent extends outwardly at an acute angle from the inner wall of the recess, whereby when the nozzle is rotated in a mounting direction on the holder, the detent flexes into and out of the holder notch, and when the nozzle is fully mounted on the holder, the detent extends into the notch, so that rotation of the nozzle in the other direction causes the detent to engage one side of the notch and break off from the remainder of the nozzle.

11. The disposable nozzle of claim 10, wherein said one side of the notch is beveled to define a knife edge for severing the detent.

12. The disposable nozzle of claim 11, wherein an inner wall of said recess includes a groove permitting flexing of the detent into the groove during mounting of the nozzle on the holder.

13. The disposable nozzle of claim 12, wherein the detent includes an inner end thinner than the remainder of the detent connecting the detent to the remainder of the nozzle body, facilitating breaking of the detent at its inner end.

* * * * *